United States Patent
Gordziel

(12) 
(10) Patent No.: US 6,287,597 B1
(45) Date of Patent: Sep. 11, 2001

(54) ANTIHISTAMINIC/DECONGESTANT COMPOSITIONS

(75) Inventor: Steven A. Gordziel, Belle Mead, NJ (US)

(73) Assignee: Carter-Wallace, Inc., New York, NY (US)

( * ) Notice: Subject to any disclaimer, the term of this patent is extended or adjusted under 35 U.S.C. 154(b) by 0 days.

(21) Appl. No.: 09/267,826

(22) Filed: Mar. 12, 1999

(51) Int. Cl.[7] .............................. A61K 9/20; A61K 31/44; A61K 31/135; A01N 43/40; A01N 33/02
(52) U.S. Cl. .......................... 424/464; 514/894; 514/853; 514/854; 514/937; 514/352; 514/653
(58) Field of Search .............................. 424/464; 514/849, 514/853, 854, 937, 352, 653

(56) References Cited

PUBLICATIONS

Rugby Labs Tri–Tannate Drug Launches (Doc # 94:20267), 1987.*
Weiler et al Randomized, double–blind, parallel groups, placebo–controlled study of efficacy and safety of Rynatan in the treatment of allergic rhinitis using an acute model Annals of Allergy 64(1);63–67, 1990.*
Genetco Tanaoral drug Launches (Doc # 94:44391), 1992.*

* cited by examiner

*Primary Examiner*—Thurman K. Page
*Assistant Examiner*—Todd D Ware
(74) *Attorney, Agent, or Firm*—Kenneth Watov; Watov & Kipnes, P.C.

(57) ABSTRACT

Tannate compositions consisting essentially of pyrilamine tannate and phenylephrine tannate which are effective when administered orally for the symptomatic relief of coryza associated with the common cold, sinusitis, allergic rhinitis and upper respiratory tract conditions are disclosed.

9 Claims, No Drawings

ANTIHISTAMINIC/DECONGESTANT COMPOSITIONS

FIELD OF INVENTION

The invention relates to novel antihistaminic/decongestant tannate compositions. The compositions contain as essential ingredients pyrilamine tannate and phenylephrine tannate.

BACKGROUND OF INVENTION

A considerable number of tannic acids occur in nature. Chemically, these acids are described as polymers of different hydroxybenzoic acids. Generally, when the term tannic acid is employed, as in the present case, the acid referred to is gallotannic acid, the internal ester of gallic acid also frequently referred to as tannin.

Tannic Acid consists of an amorphous powder, glistening scales or spongy masses varying in color from yellowish-white to light brown. Tannic acid is very soluble in water, glycerine or alcohol.

Tannic acids are usually obtained from glycosides which consist of several molecules of a tannic acid in combination with glucose.

Commercially available, tannic acid, also known as Tannin, have a complex and non-uniform chemistry usually contain from about 5% to 10% by weight water, has a molecular weight of about 1700 and is typically produced from Turkish or Chinese nutgall.

Phenylephrine, known chemically as L-m-hydroxy α [(methylamino)methyl] benzal alcohol, is a synthetic, optically active sympathomimetic amine which has one hydroxyl group on the benzene ring. The hydroxyl group is placed in the position meta to the aliphatic side chain. The meta position affords optimal activity and phenylephrine (neo-synephrine) replaced an older preparation, synephrine, in which the hydroxyl was in the para position.

Phenylephrine hydrochloride is available in the form of the levoratory isomer, a white, odorless, non-hygroscopic, crystalline compound possessing a bitter taste. Phenylephrine chloride has a melting point of 140–145° C. and is freely soluble in water and alcohol.

Pyrilamine is one of the oldest and most enduring antihistaminic drugs, known chemically as N-[(4-methoxyphenyl)methyl]-N',N'-dimethyl-N-2-pyridinyl-1,2-ethanediamine, its preparation is disclosed in U.S. Pat. No. 2,502,151 and is an oily liquid. Pyrilamines hydrochloride salt is very soluble in water and has a melting point of 143–143.5° C. whereas the maleate salt is slightly soluble in water, benzene and ether and has a melting point of 100–101°C.

Antihistamine and decongestant compounds in the form of their free bases as well as their salts, e.g. hydrochloride, citrate, maleate, tannate, etc., are well known. Antihistamines and decongestants in the form of their tannate salts are very desirable because such salts are generally stable and may be combined in such form without any untoward side effects.

Antihistaminics in the form of their tannate salts are typically prepared by reacting the antihistamine/decongestant free bases, e.g. phenylephrine and pyrilamine, with tannic acid in the presence of a volatile solvent, usually isopropanol. Typically, in the conventional isopropanol route, the antihistaminic/decongestant free bases and the tannic acid will be present in the isopropanol at a concentration of about 20% based on the weight of the reaction mixture. The reaction mixture is stirred for about one hour while maintaining the mixture at 60–70° C. The reaction mixture is cooled to room temperature and then filtered, washed with isopropanol and then vacuum dried. Alternative routes to the tannate salts are described in U.S. Pat. No. 5,599,846 and U.S. Pat. No. 5,663,415.

THE INVENTION

It has now been found that the novel combination of pyrilamine tannate and phenylephrine tannate produces a composition having sympathomimetic decongestant and antihistaminic properties superior to the use of either one of the tannate compounds alone.

The compositions of the present invention may be prepared for oral administration in the form of powders, capsules, elixirs, syrups and the preferred forms of tablets or suspensions formulated so that each 5 mL (approximately 1 teaspoon) of suspension would contain approximately 25 to 35 mg pyrilamine tannate and 3 to 8 mg phenylephrine tannate.

Tablets containing the unique tannate combination of the present invention are prepared in a conventional manner by the addition of suitable pharmaceutical carriers including fillers, diluents, lubricants and the like as well as conventional and well known binding and disintegrating agents. A typical tablet composition of the present invention may contain starch, dibasic calcium phosphate, coloring, magnesium stearate, methylcellulose, polygalacturoic acid, povidone and talc. Example 1 which follows is prepared by well known conventional tabletting techniques such as those disclosed in U.S. Pat. Nos. 3,018,221; 2,798,024 and 2,757,124 and as a three-layered tablet for oral administration.

EXAMPLE 1

| Ingredient | Milligrams per Tablet |
| --- | --- |
| Pyrilamine Tannate | 60.0 |
| Phenylephrine Tannate | 25.0[1] |
| Starch, NF | 94.0 |
| Methylcellulose, USP, 1500 cps Powder | 150 |
| Polygalactouronic Acid | 32.0 |
| Dibasic Calcium Phosphate, USP, Dihydrate Powder | 97.0 |
| Talc, USP | 5.8 |
| Magnesium Stearate, NF, Impalpable Powder | 2.6 |

[1]15% excess added during manufacture

Suspensions of the compositions of the present invention are prepared in a conventional manner such that each 5 mL (one teaspoon) contains:

| | |
| --- | --- |
| Pyrilamine Tannate | 30 mg |
| Phenylephrine Tannate | 5 mg | suspension formulations additionally contain benzoic acid, coloring, natural and artificial flavors, glycerin, kaolin, magnesium aluminum silicate, methyl paraben, pectin, purified water, saccharin, sodium hydroxide and sucrose or sorbitol.

Example 2, which follows, is illustrative of a typical suspension formulation of the present invention prepared by conventional well known compounding techniques.

EXAMPLE 2

| Ingredient | Milligrams per 5 mL |
| --- | --- |
| Pyrilamine Tannate | 30.0[2] |
| Phenylephrine Tannate | 5.0[1] |
| Pectin, USP (Medium Viscosity) | 50.0 |
| Kaolin, USP (Colloidal Powder) | 1000 |
| Magnesium Aluminum Silicate, NF, Type 1A (Veegum) | 35.0 |
| Benzoic Acid, USP | 10.0 |
| Methylparaben, NF | 5.0 |
| Sucrose, NF, Granular | 1000 |
| Saccharin Sodium, USP, Powder | 0.6 |
| Glycerin, USP | 225 |
| Flavor Black Currant Imitation | 0.91 |
| Flavor Strawberry with Other Natural Flavors | 2.28 |
| FD&C Red #3 Dye | 1.6 |
| Sodium Hydroxide Solution-50% | 3.17 |
| Purified Water, USP (Deionized) adjust to | 5 ml (6.075 gm) |

[1]15% excess added during manufacturing
[2]5% excess added during manufacturing For the purpose of this disclosure, a warm-blooded animal is a member of the animal kingdom possessed of a homeostatic mechanism and includes mammals and birds.

The dosage administered will be dependent on the age, health and weight of the recipient, kinds of concurrent treatment, if any, frequency of treatment and effect desired.

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A therapeutic composition for the symptomatic treatment of coryza associated with the common cold, sinusitis, allergic rhinitis and upper respiratory tract conditions in warm-blooded animals in need of such treatment said composition consisting of pharmaceutically effective amounts of phenylephrine tannate and pyrilamine tannate as active ingredients together with suitable pharmaceutical carriers as active ingredients together with suitable pharmaceutical carriers.

2. A therapeutic composition as claimed in claim 1 in tablet form.

3. A therapeutic composition as claimed in claim 1 in suspension form.

4. A method for symptomatically treating and relieving the distress of coryza associated with the common cold, sinusitis, allergic rhinitis and upper respiratory tract conditions in warm-blooded animals which comprises orally administering to warm-blooded animals in need of such treatment a therapeutic amount of a composition consisting of phenylephrine tannate and pyrilamine tannate as active ingredients together with suitable pharmaceutical carriers.

5. A method as claimed in claim 4 wherein said composition is in tablet form.

6. A method as claimed in claim 4 wherein said composition is a suspension.

7. A therapeutic composition as claimed in claim 2 wherein the pharmaceutically effective amounts of phenylephrine tannate and pyrilamine tannate are about 60 mg and about 25 mg, respectively, for each tablet.

8. A therapeutic composition as claimed in claim 3 wherein the pharmaceutically effective amounts of phenylephrine tannate and pyrilamine tannate are from about 25 to 35 mg and from about 3 to 8 mg, respectively, for each 5 mL volume of suspension.

9. A therapeutic composition as claimed 8 wherein the pharmaceutically effective amounts of phenylephrine tannate and pyrilamine tannate are about 30 mg and about 5 mg, respectively, for every 5 mL volume of suspension.

* * * * *